(12) United States Patent
Kordunsky et al.

(10) Patent No.: US 8,236,504 B2
(45) Date of Patent: *Aug. 7, 2012

(54) SYSTEMS AND METHODS FOR FLUORESCENCE DETECTION WITH A MOVABLE DETECTION MODULE

(75) Inventors: Igor Kordunsky, Newton, MA (US); Jeffrey A. Goldman, Acton, MA (US); Michael J. Finney, San Francisco, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/827,521

(22) Filed: Jun. 30, 2010

(65) Prior Publication Data

US 2011/0160073 A1    Jun. 30, 2011

Related U.S. Application Data

(63) Continuation of application No. 11/555,642, filed on Nov. 1, 2006, now Pat. No. 7,749,736, which is a continuation of application No. 10/431,708, filed on May 8, 2003, now Pat. No. 7,148,043.

(51) Int. Cl.
*C12Q 1/68* (2006.01)
*C12P 19/34* (2006.01)

(52) U.S. Cl. .................. 435/6.12; 435/6.1; 435/6.11

(58) Field of Classification Search ............... None
See application file for complete search history.

(56) References Cited

U.S. PATENT DOCUMENTS

| | | |
|---|---|---|
| 4,626,684 A | 12/1986 | Landa |
| 5,091,652 A | 2/1992 | Mathies et al. |
| 5,184,020 A | 2/1993 | Hearst et al. |
| 5,210,015 A | 5/1993 | Gelfand et al. |
| 5,315,375 A | 5/1994 | Allen |
| 5,415,839 A | 5/1995 | Zaun et al. |
| 5,473,437 A | 12/1995 | Blumenfeld et al. |
| 5,578,818 A | 11/1996 | Kain et al. |
| 5,585,242 A | 12/1996 | Bouma et al. |

(Continued)

FOREIGN PATENT DOCUMENTS

CN    1379236    11/2002

(Continued)

OTHER PUBLICATIONS

PCT International Preliminary Report on Patentability for PCT/US04/14566, (2005).

(Continued)

*Primary Examiner* — Young J Kim
(74) *Attorney, Agent, or Firm* — Kilpatrick Townsend & Stockton LLP

(57) ABSTRACT

A fluorescence detection apparatus for analyzing samples located in a plurality of wells in a thermal cycler and methods of use are provided. In one embodiment, the apparatus includes a support structure attachable to the thermal cycler and a detection module movably mountable on the support structure. The detection module includes one or more channels, each having an excitation light generator and an emission light detector both disposed within the detection module. When the support structure is attached to the thermal cycler and the detection module is mounted on the support structure, the detection module is movable so as to be positioned in optical communication with different ones of the plurality of wells. The detection module is removable from the support structure to allow easy replacement.

22 Claims, 7 Drawing Sheets

U.S. PATENT DOCUMENTS

| | | | |
|---|---|---|---|
| 5,595,708 | A | 1/1997 | Berndt |
| 5,736,333 | A | 4/1998 | Livak et al. |
| 5,928,907 | A | 7/1999 | Woudenberg et al. |
| 5,972,716 | A | 10/1999 | Ragusa et al. |
| 5,994,056 | A | 11/1999 | Higuchi |
| 6,015,674 | A | 1/2000 | Woudenberg et al. |
| 6,024,920 | A | 2/2000 | Cunanan |
| 6,043,880 | A | 3/2000 | Andrews et al. |
| 6,140,054 | A | 10/2000 | Wittwer et al. |
| 6,144,448 | A | 11/2000 | Mitoma |
| 6,174,670 | B1 | 1/2001 | Wittwer |
| 6,197,575 | B1 | 3/2001 | Griffith et al. |
| 6,211,989 | B1 | 4/2001 | Wulf et al. |
| 6,337,435 | B1 | 1/2002 | Chu et al. |
| 6,359,284 | B1 | 3/2002 | Hayashi et al. |
| 6,369,893 | B1 | 4/2002 | Christel et al. |
| 6,399,952 | B1 | 6/2002 | Maher et al. |
| 6,569,631 | B1 | 5/2003 | Pantoliano et al. |
| 6,818,437 | B1 | 11/2004 | Gambini et al. |
| 7,148,043 | B2 | 12/2006 | Kordunsky et al. |
| 7,749,736 | B2 * | 7/2010 | Kordunsky et al. .......... 435/91.2 |
| 2001/0046673 | A1 | 11/2001 | French et al. |
| 2002/0024026 | A1 | 2/2002 | Kaushikkar |
| 2002/0060791 | A1 | 5/2002 | Stumbo et al. |
| 2002/0064780 | A1 | 5/2002 | Gold et al. |
| 2003/0015668 | A1 | 1/2003 | Montagu |
| 2004/0014202 | A1 | 1/2004 | King et al. |

FOREIGN PATENT DOCUMENTS

| | | |
|---|---|---|
| DE | 3441179 C2 | 5/1986 |
| JP | H07-506433 | 7/1995 |
| JP | H09-508536 | 9/1997 |
| JP | 11-271227 A | 10/1999 |
| JP | 2000-121559 A | 4/2000 |
| JP | 2005-511629 | 9/2000 |
| JP | 2003-321206 | 11/2000 |
| JP | 2001-108684 A | 4/2001 |
| JP | 2001-509272 | 7/2001 |
| JP | 2001-255272 | 9/2001 |
| WO | WO 95/30139 A1 | 11/1995 |
| WO | WO 97/46707 | 12/1997 |
| WO | WO 98/53301 A2 | 11/1998 |
| WO | WO 99/12008 A1 | 3/1999 |
| WO | WO 00/31518 | 6/2000 |
| WO | WO 01/13096 A1 | 2/2001 |

OTHER PUBLICATIONS

Wittwer et al., The LightCycler.TM.: A Microvolume Multisample Fluorometer with Rapid Temperature Control, BioTechniques (Jan. 1997) vol. 22, No. 1, pp. 176-181.

European Patent Office Notice of Opposition dated Nov. 21, 2007 for EP Patent Application No. 04751790.9, 14 pages.

European Patent Office Preliminary Opinion dated May 19, 2011, 2 pages.

Patentee side written arguments with auxiliary requests dated Sep. 19, 2011, 89 pages.

Opponent's written argument dated Sep. 19, 2011, 4 pages.

Opponent's letter in reply dated Oct. 13, 2011, 7 pages.

* cited by examiner

SYSTEMS AND METHODS FOR FLUORESCENCE DETECTION WITH A MOVABLE DETECTION MODULE

CROSS-REFERENCES TO RELATED APPLICATIONS

This application is a continuation of application Ser. No. 11/555,642, filed Nov. 1, 2006, entitled "Systems and Methods For Fluorescence Detection With A Movable Detection Module," which is a continuation of application Ser. No. 10/431,708, filed May 8, 2003, entitled "Systems and Methods for Fluorescence Detection with a Movable Detection Module," now U.S. Pat. No. 7,148,043. The respective disclosures of both applications are incorporated herein by reference.

BACKGROUND OF THE INVENTION

The present invention relates in general to fluorescence detection systems and in particular to a fluorescence detection system having a movable excitation/detection module for use with a thermal cycler.

Thermal cyclers are known in the art. Such devices are used in a variety of processes for creation and detection of various molecules of interest, e.g., nucleic acid sequences, in research, medical, and industrial fields. Processes that can be performed with conventional thermal cyclers include but are not limited to amplification of nucleic acids using procedures such as the polymerase chain reaction (PCR). Such amplification processes are used to increase the amount of a target sequence present in a nucleic acid sample.

Numerous techniques for detecting the presence and/or concentration of a target molecule in a sample processed by a thermal cycler are also known. For instance, fluorescent labeling may be used. A fluorescent label (or fluorescent probe) is generally a substance which, when stimulated by an appropriate electromagnetic signal or radiation, absorbs the radiation and emits a signal (usually radiation that is distinguishable, e.g., by wavelength, from the stimulating radiation) that persists while the stimulating radiation is continued, i.e. it fluoresces. Some types of fluorescent probes are generally designed to be active only in the presence of a target molecule (e.g., a specific nucleic acid sequence), so that a fluorescent response from a sample signifies the presence of the target molecule. Other types of fluorescent probes increase their fluorescence in proportion to the quantity of double-stranded DNA present in the reaction. These types of probes are typically used where the amplification reaction is designed to operate only on the target molecule.

Fluorometry involves exposing a sample containing the fluorescent label or probe to stimulating (also called excitation) radiation, such as a light source of appropriate wavelength, thereby exciting the probe and causing fluorescence. The emitted radiation is detected using an appropriate detector, such as a photodiode, photomultiplier, charge-coupled device (CCD), or the like.

Fluorometers for use with fluorescent-labeled samples are known in the art. One type of fluorometer is an optical reader, such as described by Andrews et al. in U.S. Pat. No. 6,043,880. A sample plate containing an array of samples is inserted in the optical reader, which exposes the samples to excitation light and detects the emitted radiation. The usefulness of optical readers is limited by the need to remove the sample plate from the thermal cycler, making it difficult to monitor the progress of amplification.

One improvement integrates the optical reader with a thermal cycler, so that the sample plate may be analyzed without removing it from the thermal cycler or interrupting the PCR process. Examples of such combination devices are described in U.S. Pat. No. 5,928,907, U.S. Pat. No. 6,015,674, U.S. Pat. No. 6,043,880, U.S. Pat. No. 6,144,448, U.S. Pat. No. 6,337,435, and U.S. Pat. No. 6,369,863. Such combination devices are useful in various applications, as described, e.g., in U.S. Pat. No. 5,210,015, U.S. Pat. No. 5,994,056, U.S. Pat. No. 6,140,054, and U.S. Pat. No. 6,174,670.

Existing fluorometers suffer from various drawbacks. For instance, in some existing designs, different light sources and detectors are provided for different sample wells in the array. Variations among the light sources and/or detectors lead to variations in the detected fluorescent response from one well to the next. Alternatively, the light source and/or detector may be arranged in optical communication with more than one of the wells, with different optical paths to and/or from each well. Due to the different optical paths, the detected fluorescent response varies from one sample well to the next. To compensate for such variations, the response for each sample well must be individually calibrated. As the number of sample wells in an array increases, this becomes an increasingly time-consuming task, and errors in calibration may introduce significant errors in subsequent measurements.

In addition, existing fluorometers generally are designed such that the light sources and detectors are fixed parts of the instrument. This limits an experimenter's ability to adapt a fluorometer to a different application. For instance, detecting a different fluorescent label generally requires using a different light source and/or detector. Many existing fluorometers make it difficult for an experimenter to reconfigure light sources or detectors, thus limiting the variety of fluorescent labels that may be used.

It is also difficult to perform concurrent measurements of a number of different fluorescent labels that may be present in a sample (or in different samples). As described above, to maximize the data obtained in an assay, experimenters often include multiple fluorescent labeling agents that have different excitation and/or emission wavelengths. Each labeling agent is adapted to bind to a different target sequence, in principle allowing multiple target sequences to be detected in the same sample. Existing fluorometers, however, do not facilitate such multiple-label experiments. Many fluorometers are designed for a single combination of excitation and emission wavelengths. Others provide multiple light sources and detectors to allow detection of multiple labels; however, these configurations often allow only one label to be probed at a time because the excitation wavelength of one label may overlap the emission wavelength of another label; excitation light entering the detector would lead to incorrect results. Probing multiple labels generally cannot be done in parallel, slowing the data collection process.

Therefore, an improved fluorometer for a thermal cycler that overcomes these disadvantages would be desirable.

BRIEF SUMMARY OF THE INVENTION

Embodiments of the present invention provide fluorescence detection in a thermal cycling apparatus. According to one aspect of the invention, a fluorescence detection apparatus for analyzing samples located in a plurality of wells in a thermal cycler includes a support structure attachable to the thermal cycler and a detection module movably mountable on the support structure. The detection module includes an excitation light generator and an emission light detector, both disposed within the detection module. When the support structure is attached to the thermal cycler and the detection module is mounted on the support structure, the detection module is movable so as to be positioned in optical communication with different ones of the plurality of wells.

According to another aspect of the invention, the detection module may include two or more excitation light generators and two or more emission light detectors arranged to form two or more excitation/detection pairs. In one embodiment, the excitation/detection pairs are arranged such that each excitation/detection pair is simultaneously positionable in optical contact with a different one of the plurality of wells. In an alternative embodiment, excitation/detection pairs are arranged such that when a first one of the excitation/detection pairs is positioned in optical contact with any one of the plurality of wells, a different one of the excitation/detection pairs is not in optical contact with any one of the plurality of wells. In some embodiments, the detection module is detachably mounted on the support structure, thereby enabling a user to replace the detection module with a different detection module.

According to yet another aspect of the invention, a method for detecting the presence of a target molecule in a solution is provided. A plurality of samples is prepared, each sample containing a fluorescent probe adapted to bind to a target molecule. Each sample is placed in a respective one of a number of sample wells of a thermal cycler instrument, the thermal cycler instrument having a detection module movably mounted therein, the detection module including an excitation/detection channel, the excitation/detection channel including an excitation light generator disposed within the detection module and an emission light detector disposed within the detection module. The thermal cycler instrument is used to stimulate a reaction, and the sample wells are scanned to detect a fluorescent response by moving the detection module and activating the excitation/detection channel. During the scanning, the detection module is moved such that the excitation/detection channel is sequentially positioned in optical communication with each of the plurality of sample wells. Where the detection module includes multiple excitation/detection pairs or channels, channels may be active in parallel or sequentially.

The following detailed description together with the accompanying drawings will provide a better understanding of the nature and advantages of the present invention.

DETAILED DESCRIPTION OF THE INVENTION

Figure 1:
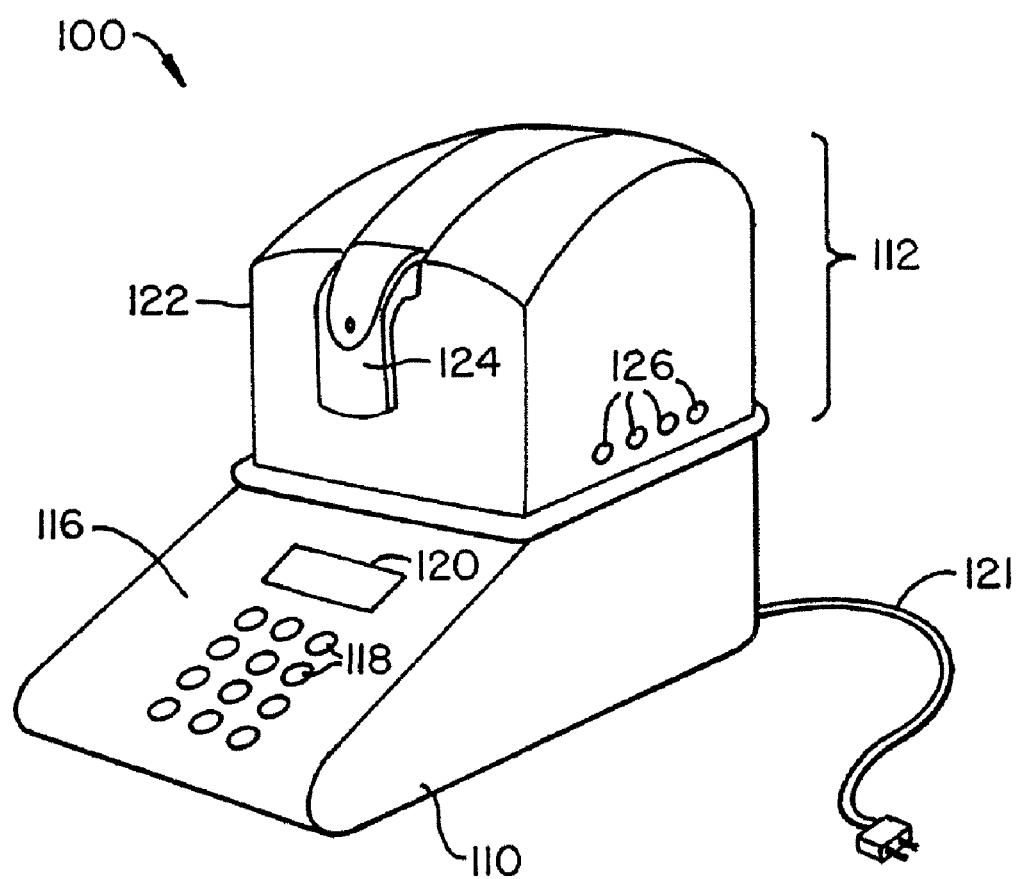
FIG. 1 is a perspective view of a thermal cycling apparatus according to an embodiment of the present invention.

An exemplary apparatus embodiment of the present invention will be described with reference to the accompanying drawings, in which like reference numerals indicate corresponding parts. Methods of using the apparatus will also be described. It is to be understood that embodiments shown and described herein are illustrative and not limiting of the invention.

I. Exemplary Apparatus

FIG. 1 is a perspective view of a thermal cycling apparatus 100 according to an embodiment of the present invention. Apparatus 100 consists of a base unit 110 and a lid assembly 112. Base unit 110, which may be of conventional design, provides power and control functions for a thermal cycling process via conventional electronic components (not shown), such as programmable processors, clocks, and the like. Base unit 110 also provides a user interface 116 that may include a keypad 118 and an LCD display screen 120, enabling a user to control and monitor operation of the thermal cycler. Base unit 110 connects to an external power source (e.g., standard 120 V ac power) via a power cable 121. Some examples of base unit 110 include the DNA Engine®, Dyad™, and Tetrad™ thermal cyclers sold by MJ Research, Inc., assignee of the present application.

Lid assembly 112 includes a sample unit and a fluorescence detection apparatus, disposed within a lid 122; these components will be described below. Lid 122 has a handle 124 to aid in its placement on and removal from base unit 110, and ventilation holes 126. Lid 122 provides optical and thermal isolation for the components inside lid assembly 112.

Figure 2:
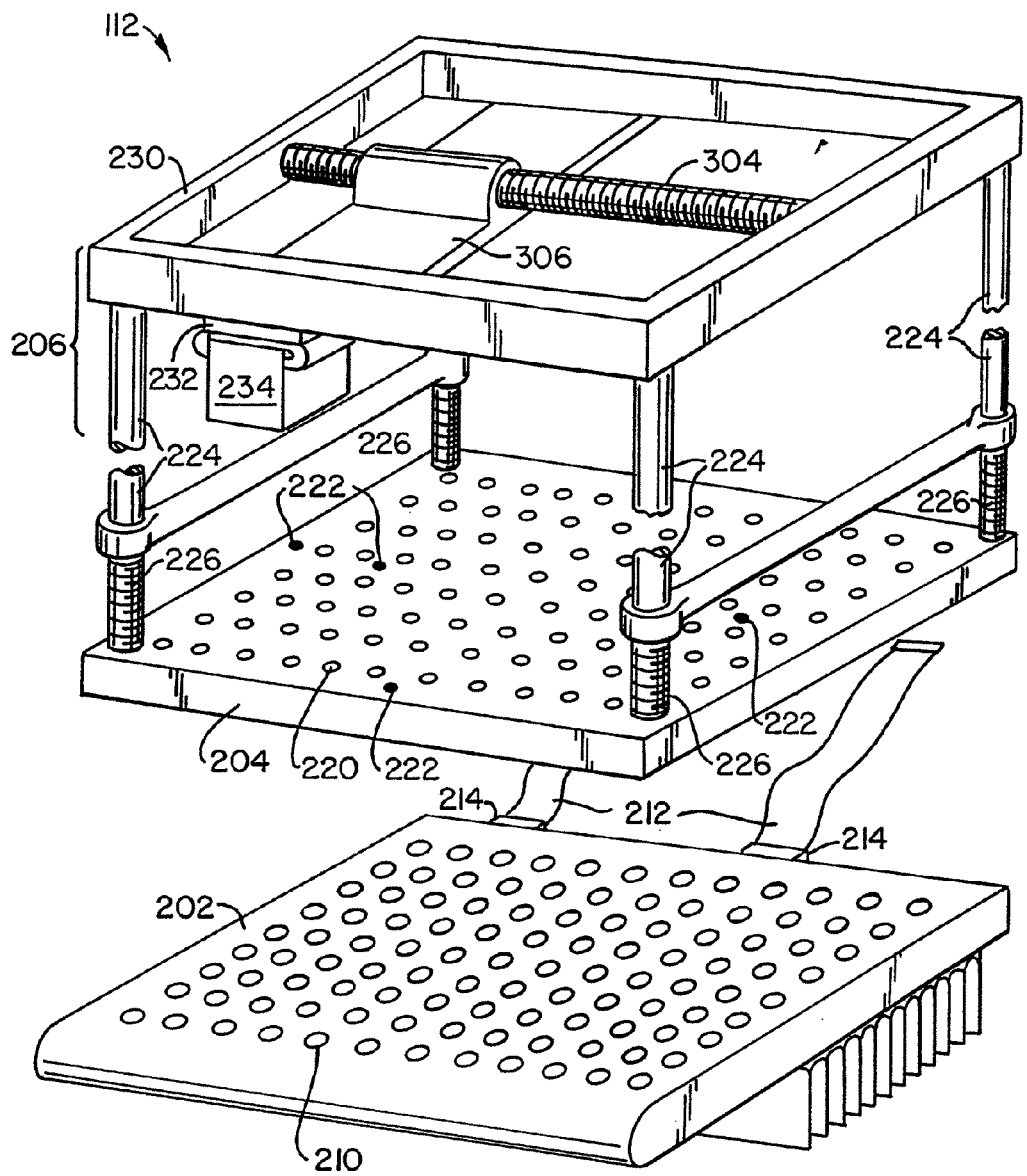
FIG. 2 is an exploded view of a lid assembly for a thermal cycling apparatus according to an embodiment of the present invention.

FIG. 2 is an exploded view of the inside of lid assembly 112. Shown are a sample unit 202, a lid heater 204, and a fluorometer assembly 206. Sample unit 202 contains a number of sample wells 210 arranged in a regular array (e.g., an 8×12 grid). In one embodiment, each sample well 210 holds a removable reaction vessel (not shown), such as a tube, that contains a nucleic acid sample to be tested, together with appropriate PCR reactants (buffers, primers and probes, nucleotides, and the like) including at least one fluorescent label or probe adapted to bind to or otherwise respond to the presence of a target nucleic acid sequence. The reaction vessels are advantageously provided with transparent sample caps (not shown) that fit securely over the tops of the vessels to prevent cross-contamination of samples or spillage during handling. Reaction vessels may also be sealed in other ways, including the use of films such as Microseal®B (made by MJ Research, Inc.), wax products such as Chill-out™ (made by MJ Research, Inc.), or mineral oil. In an alternative configuration, a removable sample tray (not shown) that holds one or more distinct samples at locations corresponding to sample wells 210 is used. The sample tray may also be sealed in any of the ways described above.

Sample unit 202 also includes heating elements (e.g., Peltier-effect thermoelectric devices), heat exchange elements, electrical connection elements for connecting the heating elements to base unit 110, and mechanical connection elements. These components (not shown) may be of conventional design. Sample unit 202 also provides electrical connections for lid heater 204 and fluorometer assembly 206 via multiwire cables 212, which are detachably connected to connectors 214.

Lid heater 204 has holes 220 therethrough, matching the size and spacing of the sample wells 210, and electronically controlled heating elements (not shown). Lid heater 204 is coupled to lid 122. The coupling mechanism (not shown) is advantageously movable (e.g., lid heater 204 may be attached to lid 122 by a hinge) in order to provide access to fluorometer assembly 206 when lid 122 is removed from sample unit 202. When lid 122 is in place on sample unit 202, supports 224 hold lid heater 204 in position. Lower portions 226 of supports 224 are advantageously designed to compress lid heater 204 toward sample unit 202, thereby reducing the possibility of sample evaporation during operation of apparatus 100. This compression also allows reaction vessels of different sizes to be used. Lid heater 204 is used to control the temperature of the sample caps (or other sealants) of reaction vessels sample wells 210, in order to prevent condensation from forming on the caps during thermal cycling operation.

Lid heater 204 advantageously includes one or more calibration elements 222 positioned between selected ones of holes 220 or in other locations away from the holes, such as near the periphery of 11d heater 204. Calibration elements 222 provide a known fluorescence response and may be used to calibrate fluorescence detectors in fluorometer assembly 206. Calibration elements 222 may be made, e.g., of a fluorescent coating on a glass or plastic substrate, or they may consist of a plastic with a dye impregnated in it, fluorescent glass, or a fluorescent plastic such as polyetherimide (PEI). Neutral-density or other types of filters may be placed over the fluorescent material in order to avoid saturating the fluorescence detectors. In general, any material may be used, provided that its fluorescence characteristics are sufficiently stable over time with the application of light (photo-bleaching) and heat. To the extent practical, the effect of temperature on the fluorescence response is advantageously minimized. Where multiple calibration elements 222 are provided, different materials may be used for different ones of the calibration elements. In an alternative embodiment, lid heater 204 may be omitted, and calibration elements 222 may be disposed on the surface of sample unit 202.

Sample unit 202 and lid heater 204 may be of conventional design. Examples of suitable designs include sample unit and lid heater components of the various Alpha™ modules sold by MJ Research, Inc., assignee of the present application.

Fluorometer assembly 206 includes a support frame or platform 230 fixedly mounted inside lid 122. Movably mounted on the underside of support frame 230 is a shuttle 232, which holds a detection module 234. Shuttle 232 is movable in two dimensions so as to position detection module 234 in optical communication with different ones of the sample wells 210 in sample unit 202 through the corresponding holes 220 in lid heater 204. Support frame 230 and supports 224 are advantageously dimensioned such that when lid 122 is positioned in base unit 110 and closed, detection module 234 is held in close proximity to lid heater 204; one of skill in the art will appreciate that this arrangement reduces light loss between the sample wells and the detection module.

Figure 3:
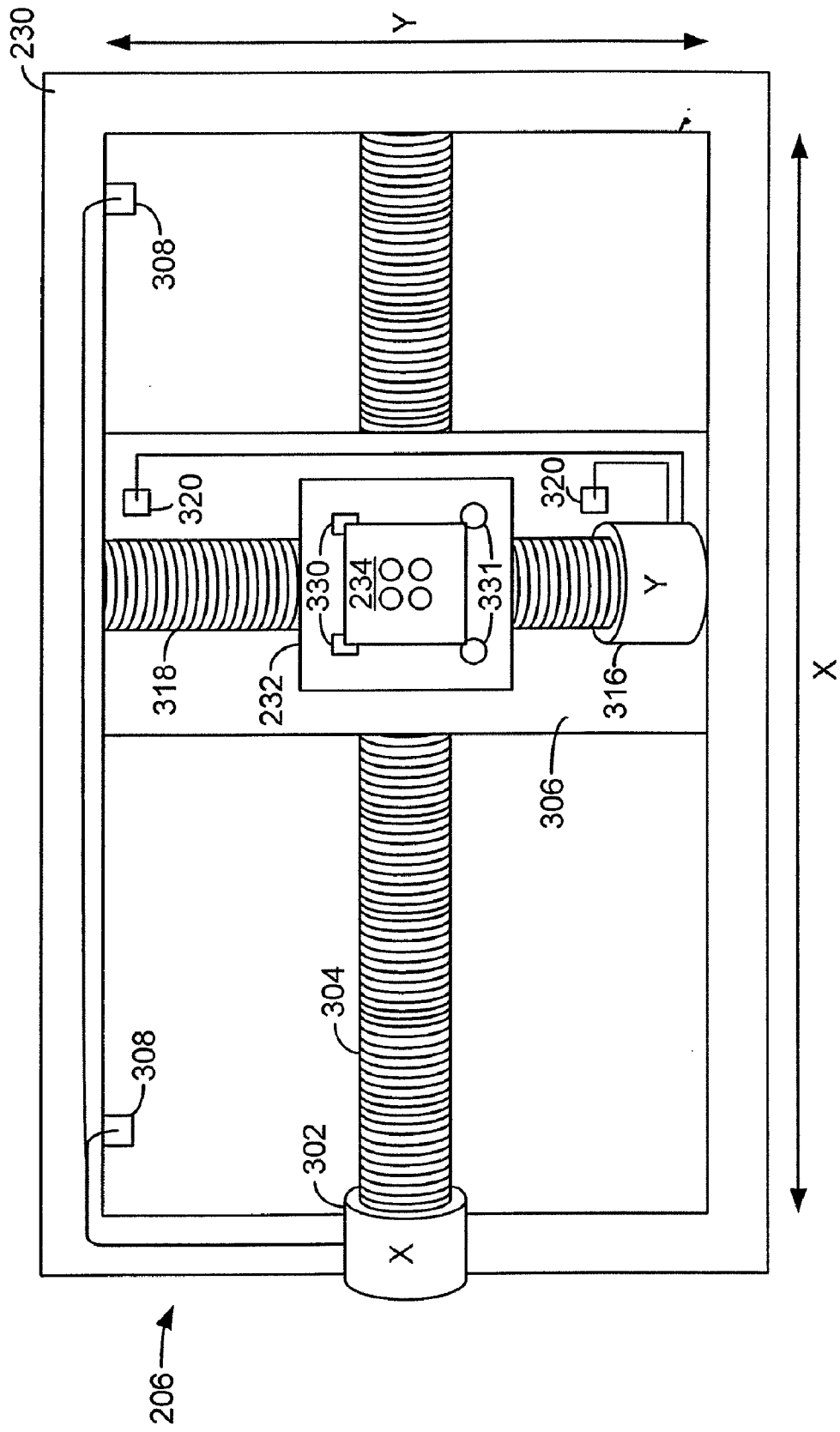
FIG. 3 is a bottom view of a fluorometer assembly for a thermal cycling apparatus according to an embodiment of the present invention.

FIG. 3 is a bottom view of fluorometer assembly 206, showing a movable mounting of shuttle 232 and detection module 234. In this embodiment, translation stages driven by stepper motors are used to move the shuttle 232, to which detection module 234 is detachably coupled, to a desired position. Specifically, support platform 230 has an x-axis stepper motor 302 and a lead screw 304 attached thereto. Stepper motor 302 operates to turn lead screw 304, thereby moving a translation stage 306 along the x direction (indicated by arrow). Limit switches 308 are advantageously provided to restrict the motion of translation stage 306 to an appropriate range, large enough to allow detection module 234 to be placed in optical contact with any of the wells while preventing translation stage 306 from contacting other system components, such as stepper motor 302.

Translation stage 306 has a y-axis stepper motor 316 and a lead screw 318 mounted thereon. Stepper motor 316 operates to turn lead screw 318, thereby moving shuttle 232 along the y direction (indicated by arrow). Limit switches 320 are advantageously provided to restrict the motion of shuttle 232 to an appropriate range, large enough to allow detection module 234 to be placed in optical contact with any of the wells, while preventing shuttle 232 from contacting other system components, such as stepper motor 316.

Stepper motors 302, 316, lead screws 304, 318, and limit switches 308, 320 may be of generally conventional design. It will be appreciated that other movable mountings may be substituted. For example, instead of directly coupling the motors to the lead screws, indirect couplings such as chain drives or belt drives may be used. Chain drives, belt drives, or other drive mechanisms may also be used to position the detection module without lead screws, e.g., by attaching a translation stage to the chain, belt, or other drive mechanism. Other types of motors, such as servo motors or linear motors, may also be used. Different drive mechanisms may be used for different degrees of freedom.

Shuttle 232 holds detection module 234 via connectors 330, 331. Connectors 330, 331 which may vary in design, are configured to support and align detection module 234 on the underside of shuttle 232. The connectors are advantageously adapted to allow easy insertion and removal of detection module 234, to facilitate replacement of the detection module. In one embodiment, connectors 330 provide mounting for a cylindrical member (not shown) that pivotably holds an edge of detection module 234, while connectors 331 include ball plungers mounted on shuttle 232 that are insertable into corresponding receptacles on detection module 234. Electrical connections (not shown) between shuttle 232 and detection module 234 may also be provided, as will be described below.

Figure 4:
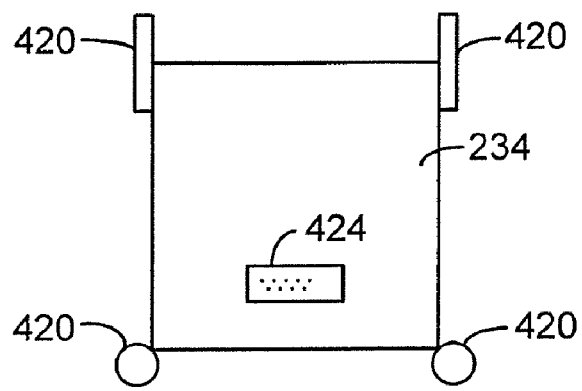
FIG. 4 is a top view of detection module according to an embodiment of the present invention.

FIG. 4 is a top view of detection module 234. Detection module 234 includes fittings 420 that couple to corresponding connectors 330 on the underside of shuttle 232, thereby securing detection module 234 in place so that it moves as a unit with shuttle 232. Detection module 234 also includes an electrical connector 424 that couples to a corresponding electrical connector on the underside of shuttle 232, thereby allowing control and readout signals to be provided to and obtained from detection module 234.

Figure 5A:
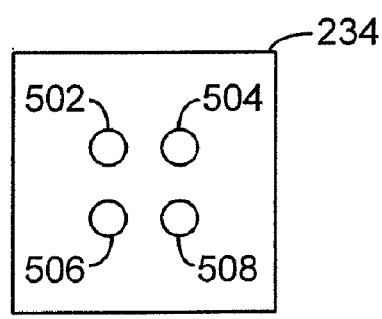
FIGS. 5A-B are bottom views of detection modules according to alternative embodiments of the present invention.

FIG. 5A is a bottom view of one embodiment of detection module 234, showing four openings 502, 504, 506, 508 for four independently controlled fluorescent excitation/detection channels (also referred to as "excitation/detection pairs") arranged inside the body of detection module 234. Examples of excitation/detection channels will be described below. The spacing of openings 502, 504, 506, 508 corresponds to the spacing of sample wells 210. Thus, when opening 502 is placed in optical communication with one of the sample wells 210, openings 504, 506, and 508 are each in optical communication with a different one of the sample wells 210. Openings 502, 504, 506, 508 may simply be holes through the bottom surface of detection module 234, or they may be made of any substance that has a high degree of transparency to the excitation and detection light wavelengths of their respective channels.

Figure 5B:
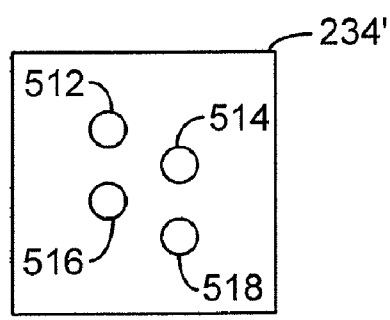

FIG. 5B is a bottom view of a detection module 234' according to an alternative embodiment of the invention. In this embodiment, four openings 512, 514, 516, 518 are provided, but they are arranged in a staggered fashion so that only one opening at a time may be in optical communication with any of the sample wells. This configuration is useful for reducing cross-talk between the excitation/detection pairs.

Figure 6:
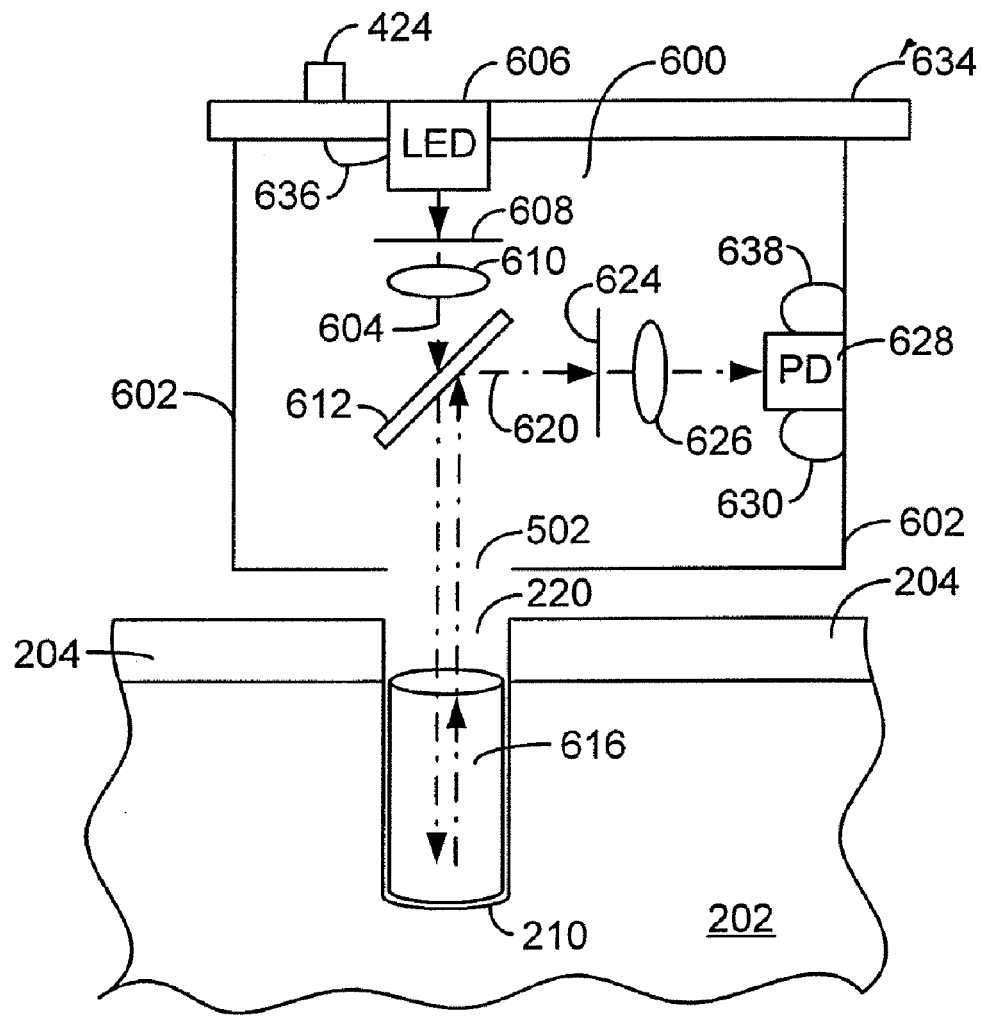
FIG. 6 is a schematic diagram of an excitation/detection pair for a detection module according to an embodiment of the present invention.

FIG. 6 is a schematic diagram illustrating a configuration of optical elements for an excitation/detection channel (or excitation/detection pair) 600 according to an embodiment of the invention. Detection module 234 may include one or more instances of excitation/detection pair 600, each of which provides an independent fluorescence detection channel. Excitation/detection pair 600 is arranged inside opaque walls 602, which provide optical isolation from other excitation/detection pairs that may be included in detection module 234, as well as from external light sources. An excitation light path 604 includes a light-emitting diode (LED) or other light source 606, a filter 608, a lens 610, and a beam splitter 612. A detection light path 620 includes beam splitter 612, a filter 624, a lens 626, and a photodiode or other photodetector 628. Beam splitter 612 is advantageously selected to be highly transparent to light of the excitation wavelength and highly reflective of light at the detection (fluorescent response) wavelength.

The components of excitation light path 604 are arranged to direct excitation light of a desired wavelength into a reaction vessel 616 held in a sample well 210 of sample block 202. The desired wavelength depends on the particular fluorescent labeling agents included in reaction vessel 616 and is controlled by selection of an appropriate LED 606 and filter 608. Optical communication between the excitation/detection pair 600 and reaction vessel 616 is provided by opening 502 in opaque walls 602 and a hole 220 through lid heater 204, as described above. To maximize light transmission to and from excitation/detection pair 600, the space between opening 502 and lid heater 204 is advantageously made small during operation.

Excitation light that enters reaction vessel 616 excites the fluorescent label or probe therein, which fluoresces, thereby generating light of a different wavelength. Some of this light exits reaction vessel 616 on detection light path 620 and passes through opening 502. Beam splitter 612 directs a substantial portion of the fluorescent light through filter 624, which filters out the excitation frequency, and lens 626, which focuses the light onto the active surface of photodiode 628. Photodiode 628 generates an electrical signal in response to the incident light. This electrical signal is transmitted by a readout signal path 630 to circuit board 634, which routes the signal to electrical connector 424 for readout. Circuit board 634 and/or signal path 630 may also include other components, such as pre-amplifiers, for shaping and refining the electrical signal from photodiode 628.

LED 606 and photodiode 628 may be controlled by signals received via connector 424, as indicated by respective control signal paths 636, 638. Control signals for LED 606 may operate to activate and deactivate LED 606 at desired times; control signals for photodiode 628 may operate to activate and deactivate photodiode 628 at desired times, adjust a gain parameter, and so on.

While FIG. 6 shows one excitation/detection pair 600, it is to be understood that an embodiment of detection module 234 may contain any number of such pairs, each of which is advantageously in optical isolation from the others and has its own opening for optical communication with the sample wells (e.g., openings 504, 506, 508 of FIG. 5). The various excitation/detection pairs are independently controlled and independently read out, but their respective control and readout paths may all be coupled to circuit board 634.

The configuration of excitation/detection pairs may be varied from that shown, and the excitation and detection light paths may include additional components, fewer components, or any combination of desired components. The optics may be modified as appropriate for a particular application (e.g., the optical path may be shorter in embodiments where lid heater 204 is not included) and use any number and combination of components including but not limited to lenses, beam splitters, mirrors, and filters. While LEDs provide a compact and reliable light source, use of other types of coherent or incoherent light sources, such as laser diodes, flash lamps, and so on, is not precluded. Similarly, the detectors are not limited to photodiodes; any type of photodetector may be substituted, including photomultipliers and charge-coupled devices (CCDs). Each excitation/detection pair is advantageously configured as a self-contained assembly, requiring only external electrical connections to make it operational. Because the length of the excitation and detection optical paths do not vary from one experiment to the next, it is desirable to fixedly mount and optimize the various optical components of each excitation/detection pair 600 inside detection module 234 during manufacture so that further adjustments during operation are not required.

Figure 7:
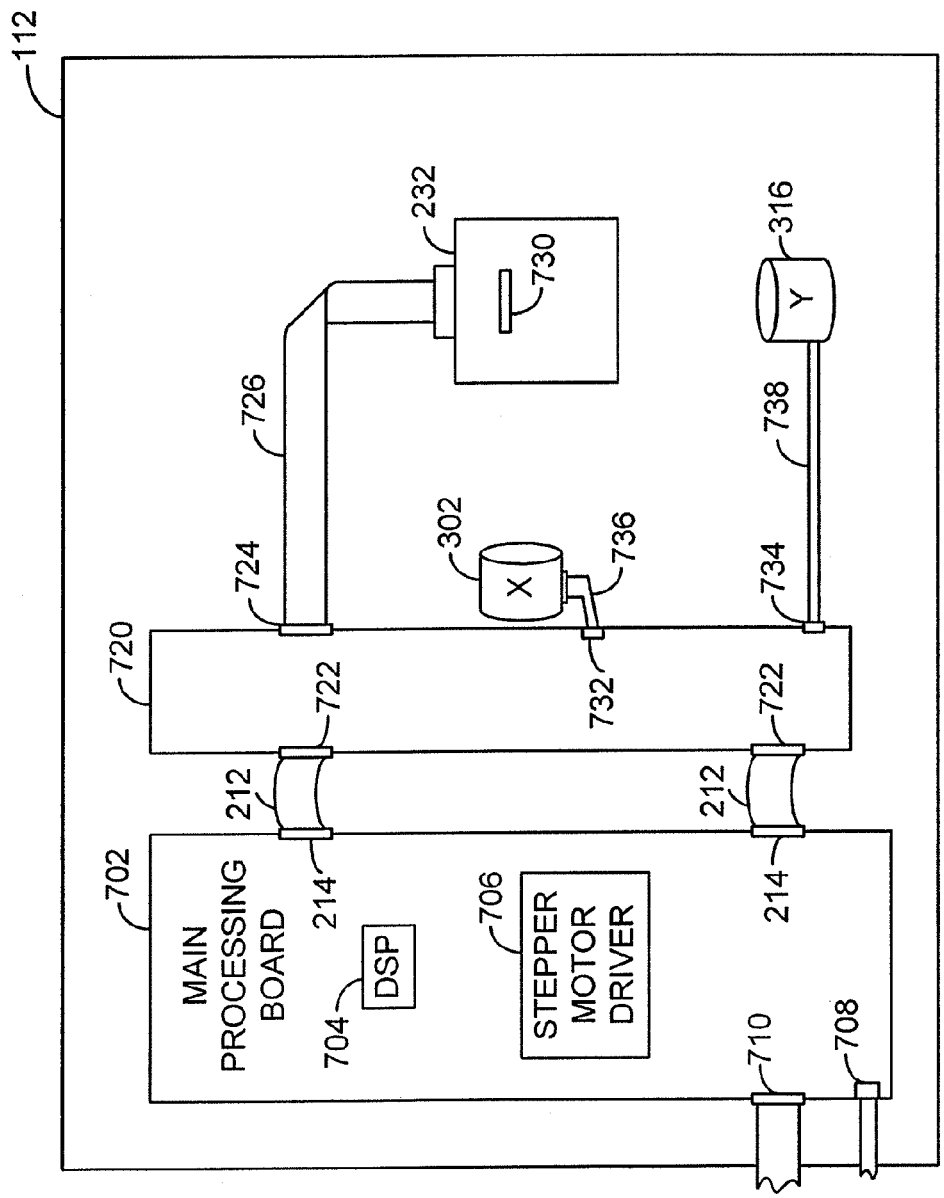
FIG. 7 is a block diagram illustrating electrical connections for a lid assembly for a thermal cycling apparatus according to an embodiment of the present invention.

FIG. 7 is a block diagram illustrating electrical connections for lid assembly 112. A main processing board 702 is mounted in lid assembly 112. Main processing board 702 includes a primary signal processor 704, a stepper motor driver unit 706, a connection 708 for electrical power, and a connection 710 for an external computer (e.g., a personal computer, or PC). Main processing board 702 also provides connectors 214 for cables 212 that provide transmission of electrical signals to and from lid 122.

Lid 122 includes a secondary processing board 720 that facilitates communication between main processing board 702 and stepper motors 302, 316, as well as shuttle 232. Secondary processing board 720 includes connectors 722 for cables 212, a connector 724 that connects a cable 726 to shuttle 232, and connectors 732 and 734 for cables 736, 738 that provide control signals to the x and y stepper motors 302, 316. Routing paths (not shown) in secondary processing board 720 establish appropriate signal connections between the various connectors.

Cable 726 is used to communicate control signals for detection module 234, such as activating and deactivating individual light sources, and to receive signals from the photodetectors included in detection module 234. Electrical connector 730 is provided on shuttle 232 for passing signals to and from detection module 234. Electrical connector 730 accepts the mating connector 424 on the top surface of detection module 234 when detection module 234 is mounted on shuttle 232. In an alternative embodiment, cable 726 may attach directly to detection module 234.

As mentioned above, main processing board 702 provides a connection 710 to an external computer (not shown). The external computer may be used to control the motion of shuttle 232 and the operation of detection module 234, as well as for readout and analysis of fluorometry data obtained from detection module 234.

As described above, detection module 234 is designed to be self-contained and detachable from shuttle 232. This allows for a reconfigurable fluorometry system, in which an experimenter is able to change detection modules as desired to perform different measurements. For instance, different detection modules may be optimized for different fluorescent labeling agents (or combinations of agents). If the experimenter wishes to study a different agent, she simply installs the appropriate detection module. Installation is a matter of attaching electrical connector 424 and mechanical connectors 420 on the top of the desired detection module 234 to corresponding connectors on the underside of shuttle 234. In some embodiments, the connectors are designed such that the electrical connection is made automatically as the mechanical connection is engaged. As noted above, lid heater 204 is advantageously movably mounted so as to allow access to fluorescence assembly 230, thereby allowing experimenters to change detection modules.

It will be appreciated that the apparatus described herein is illustrative and that variations and modifications are possible. For instance, the base and sample unit may be designed as an integrated system or separated further into smaller modular components. The fluorometer assembly need not be attached or otherwise integrated into the lid, so long as it is mountable in a fixed position relative to the sample wells. Any mechanism may be used to make the detection module movable so as to position it in optical communication with different ones of the sample wells, not limited to translation stages or stepper motors. The detection module may include any number (one or more) of excitation/detection pairs operable as independent detection channels, and different pairs may be designed to detect the same fluorescent probe or different fluorescent probes. In one alternative embodiment, the detection module includes a row of excitation/detection pairs with optical windows arranged to correspond to a row of the sample array, and the detection module is made movable in one direction to interrogate different columns of the array.

The external computer is also optional, and any of its functions may be integrated into the thermal cycler device; conversely, control functions for the thermal cycler may be implemented to operate on the external computer, thereby providing a single control device for the entire apparatus. In one embodiment, the external computer is used to control the position of detection module 234 with respect to the sample wells and operations of the light source(s) and detector(s). In addition, any external computer may be special purpose control and signal-processing devices as well as a general-purpose computer such as a PC.

II. Methods of Use

The apparatus described herein can be used to detect the amount of amplification product generated in an amplification reaction by detecting the amount of fluorescence. Various amplification techniques can be used to quantify target sequences present in DNA or RNA samples. Such techniques, which involve enzymatic synthesis of nucleic acid amplicons (copies) that contain a sequence that is complementary to the sequence being amplified, are well known in the art and widely used. These include, but are not limited to the polymerase chain reaction (PCR), RT-PCR, strand displacement amplification (SDA), transcription based amplification reactions, ligase chain reaction (LCR), and others (see, e.g. Dieffenbach & Dveksler, *PCR Primer: A Laboratory Manual*, 1995; U.S. Pat. Nos. 4,683,195 and 4,683,202; *PCR Protocols: A Guide to Methods and Applications*, Innis et al., eds, 1990; Walker, et al., *Nucleic Acids Res.* 20(7):1691-6, 1992; Walker, *PCR Methods Appl* 3(1):1-6, 1993; Phyffer, et al., *J. Clin. Microbiol.* 34:834-841, 1996; Vuorinen, et al., *J. Clin. Microbiol.* 33:1856-1859, 1995; Compton, *Nature* 350(6313):91-2, 1991; Lisby, *Mol. Biotechnol.* 12(1):75-991999; Hatch et al., *Genet. Anal.* 15(2):35-40, 1999; and Iqbal et al., *Mol. Cell. Probes* 13(4):315-320; 1999). Nucleic acid amplification is especially beneficial when the amount of target sequence present in a sample is very low. By amplifying the target sequence and detecting the amplicon synthesized, the sensitivity of an assay may be vastly improved, since fewer copies of the target sequence are needed at the beginning of the assay to better ensure detection of nucleic acid in the sample belonging to the organism or virus of interest.

Measurement of amplification products can be performed after the reaction has been completed or in real time (i.e., substantially continuously). If measurement of accumulated amplified product is performed after amplification is complete, then detection reagents (e.g., fluorescent probes) can be added after the amplification reaction. Alternatively, probes can be added to the reaction prior to or during the amplification reaction, thus allowing for measurement of the amplified products either after completion of amplification or in real time. If amplified products are measured in real time, initial copy number can be estimated by determining the cycle number at which the signal crosses a threshold and projecting back to initial copy number, assuming exponential amplification.

A. Fluorescent Probes

A number of formats are available that make use of fluorescent probes. These formats are often based on fluorescence resonance energy transfer (FRET) and include molecular beacon, and TaqMan® probes. FRET is a distance-dependent interaction between a donor and acceptor molecule. The donor and acceptor molecules are fluorophores. If the fluorophores have excitation and emission spectra that overlap, then in close proximity (typically around 10-100 angstroms) the excitation of the donor fluorophore is transferred to the acceptor fluorophore. As a result, the lifetime of the donor molecule is decreased and its fluorescence is quenched, while the fluorescence intensity of the acceptor molecule is enhanced and depolarized. When the excited-state energy of the donor is transferred to a non-fluorophore acceptor, the fluorescence of the donor is quenched without subsequent emission of fluorescence by the acceptor. In this case, the acceptor functions as a quenching reagent.

One FRET-based format for real-time PCR uses DNA probes known as "molecular beacons" (see, e.g., Tyagi et al., *Nat. Biotech.* 16:49-53, 1998; U.S. Pat. No. 5,925,517). Molecular beacons have a hairpin structure wherein the quencher dye and reporter dye are in intimate contact with each other at the end of the stem of the hairpin. Upon hybridization with a complementary sequence, the loop of the hairpin structure becomes double stranded and forces the quencher and reporter dye apart, thus generating a fluorescent signal. A related detection method uses hairpin primers as the fluorogenic probe (Nazarenko et al., *Nucl. Acid Res.* 25:2516-2521, 1997; U.S. Pat. No. 5,866,336; U.S. Pat. No. 5,958,700). The PCR primers can be designed in such a manner that only when the primer adopts a linear structure, i.e., is incorporated into a PCR product, is a fluorescent signal generated.

Amplification products can also be detected in solution using a fluorogenic 5' nuclease assay, a TaqMan assay. See Holland et al., *Proc. Natl. Acad. Sci. U.S.A.* 88: 7276-7280, 1991; U.S. Pat. Nos. 5,538,848, 5,723,591, and 5,876,930. The TaqMan probe is designed to hybridize to a sequence within the desired PCR product. The 5' end of the TaqMan probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. The excising of the 5' fluorophore results in an increase in fluorescence which can be detected.

In addition to the hairpin and 5'-nuclease PCR assay, other formats have been developed that use the FRET mechanism. For example, single-stranded signal primers have been modified by linkage to two dyes to form a donor/acceptor dye pair in such a way that fluorescence of the first dye is quenched by the second dye. This signal primer contains a restriction site (U.S. Pat. No. 5,846,726) that allows the appropriate restriction enzyme to nick the primer when hybridized to a target. This cleavage separates the two dyes and a change in fluorescence is observed due to a decrease in quenching. Non-nucleotide linking reagents to couple oligonucleotides to ligands have also been described (U.S. Pat. No. 5,696,251).

Other amplification reactions that can be monitored using a fluorescent reading include those that are quantified by measuring the amount of DNA-binding dye bound to the amplification product. Such assays use fluorescent dyes, e.g., ethidium bromide or SYBR Green I (Molecular Probes, Inc., Eugene, Oreg.; U.S. Pat. Nos. 5,436,134 and 5,658,751) that exhibit increased fluorescence when intercalated into DNA (see, e.g., U.S. Pat. Nos. 5,994,056 and 6,171,785). Use of SYBR Green I for this purpose is also described in Morrison et al. (Biotechniques 24, 954-962, 1998). An increase in fluorescence reflects an increase in the amount of double-stranded DNA generated by the amplification reaction.

Other fluorescent probes include inorganic molecules, multi-molecular mixtures of organic and/or inorganic molecules, crystals, heteropolymers, and the like. For example, CdSe—CdS core-shell nanocrystals enclosed in a silica shell may be easily derivatized for coupling to a biological molecule (Bruchez et al. (1998) Science, 281: 2013-2016). Similarly, highly fluorescent quantum dots (zinc sulfide-capped cadmium selenide) have been covalently coupled to biomolecules for use in ultrasensitive biological detection (Warren and Nie (1998) Science, 281: 2016-2018).

Multiplex assays may also be performed using apparatus 100. Multiplex PCR results in the amplification of multiple polynucleotide fragments in the same reaction. See, e.g., PCR PRIMER, A LABORATORY MANUAL (Dieffenbach, ed. 1995) Cold Spring Harbor Press, pages 157-171. For instance, different target templates can be added and amplified in parallel in the same reaction vessel. Multiplex assays typically involve the use of different fluorescent labels to detect the different target sequences that are amplified.

B. PCR Conditions and Components

Exemplary PCR reaction conditions typically comprise either two or three step cycles. Two step cycles have a denaturation step followed by a hybridization/elongation step. Three step cycles comprise a denaturation step followed by a hybridization step followed by a separate elongation step. The polymerase reactions are incubated under conditions in which the primers hybridize to the target sequences and are extended by a polymerase. The amplification reaction cycle conditions are selected so that the primers hybridize specifically to the target sequence and are extended.

Successful PCR amplification requires high yield, high selectivity, and a controlled reaction rate at each step. Yield, selectivity, and reaction rate generally depend on the temperature, and optimal temperatures depend on the composition and length of the polynucleotide, enzymes and other components in the reaction system. In addition, different temperatures may be optimal for different steps. Optimal reaction conditions may vary, depending on the target sequence and the composition of the primer. Thermal cyclers such as apparatus 100 provide the necessary control of reaction conditions to optimize the PCR process for a particular assay. For instance, apparatus 100 may be programmed by selecting temperatures to be maintained, time durations for each cycle, number of cycles, and the like. In some embodiments, temperature gradients may be programmed so that different sample wells may be maintained at different temperatures, and so on.

Fluorescent oligonucleotides (primers or probes) containing base-linked or terminally-linked fluors and quenchers are well-known in the art. They can be obtained, for example, from Life Technologies (Gaithersburg, Md.), Sigma-Genosys (The Woodlands, Tex.), Genset Corp. (La Jolla, Calif.), or Synthetic Genetics (San Diego, Calif.). Base-linked fluors are incorporated into the oligonucleotides by post-synthesis modification of oligonucleotides that are synthesized with reactive groups linked to bases. One of skill in the art will recognize that a large number of different fluorophores are available, including from commercial sources such as Molecular Probes, Eugene, Oreg. and other fluorophores are known to those of skill in the art. Useful fluorophores include: fluorescein, fluorescein isothiocyanate (FITC), carboxy tetrachloro fluorescein (TET), NHS-fluorescein, 5 and/or 6-carboxy fluorescein (FAM), 5-(or 6-) iodoacetamidofluorescein, 5-{[2 (and 3)-5-(Acetylmercapto)-succinyl] amino}fluorescein (SAMSA-fluorescein), and other fluorescein derivatives, rhodamine, Lissamine rhodamine B sulfonyl chloride, Texas red sulfonyl chloride, 5 and/or 6 carboxy rhodamine (ROX) and other rhodamine derivatives, coumarin, 7-amino-methyl-coumarin, 7-Amino-4-methylcoumarin-3-acetic acid (AMCA), and other coumarin derivatives, BODIPY™ fluorophores, Cascade Blue™ fluorophores such as 8-methoxypyrene-1,3,6-trisulfonic acid trisodium salt, Lucifer yellow fluorophores such as 3,6-Disulfonate-4-amino-naphthalimide, phycobiliproteins derivatives, Alexa fluor dyes (available from Molecular Probes, Eugene, Oreg.) and other fluorophores known to those of skill in the art. For a general listing of useful fluorophores, see also Hermanson, G. T., BIOCONJUGATE TECHNIQUES (Academic Press, San Diego, 1996).

The primers for the amplification reactions are designed according to known algorithms. For example, algorithms implemented in commercially available or custom software can be used to design primers for amplifying the target sequences. Typically, the primers are at least 12 bases, more often 15, 18, or 20 bases in length. Primers are typically designed so that all primers participating in a particular reaction have melting temperatures that are within 5° C., and most preferably within 2° C. of each other. Primers are further designed to avoid priming on themselves or each other. Primer concentration should be sufficient to bind to the amount of target sequences that are amplified so as to provide an accurate assessment of the quantity of amplified sequence. Those of skill in the art will recognize that the amount of concentration of primer will vary according to the binding affinity of the primers as well as the quantity of sequence to be bound. Typical primer concentrations will range from 0.01 µM to 0.5 µM.

One of skill in the art will further recognize that it is desirable to design buffer conditions to allow for the function of all reactions of interest. Thus, buffer conditions can be designed to support the amplification reaction as well as any enzymatic reactions associated with producing signals from probes. A particular reaction buffer can be tested for its ability to support various reactions by testing the reactions both individually and in combination. The concentration of components of the reaction such as salt, or magnesium can also affect the ability of primers or detection probes to anneal to the target nucleic acid. These can be adjusted in accordance with guidance well known in the art, e.g., Innis et al., supra.

C. Exemplary PCR Process

Figure 8:
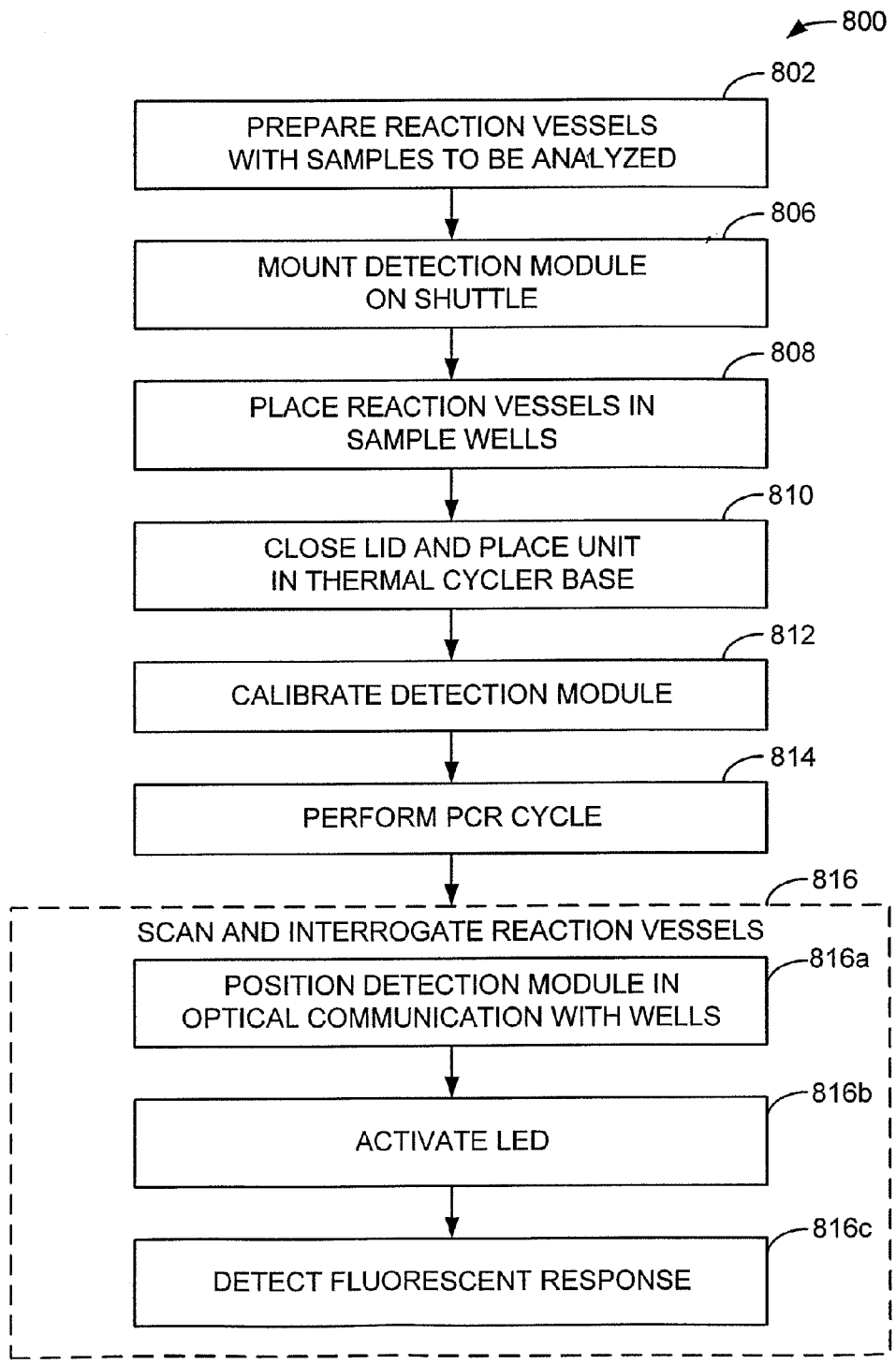
FIG. 8 is a flow diagram of a process for using a thermal cycler having a fluorescence detection system according to an embodiment of the present invention.

FIG. 8 is a flow chart of a nucleic acid amplification and measurement process 800 using apparatus 100. In this example, apparatus 100 controls a PCR amplification process and detects the presence of multiple target sequences in the nucleic acid samples.

At step 802, reaction vessels 616 are prepared. Preparation includes placing reaction components into the vessels and sealing the vessels to prevent spillage or cross-contamination. The reaction components include buffer, target nucleic acid, appropriate primers and probes, nucleotides, polymerases, as well as optional additional components. In one embodiment, four fluorescent probes are included, each adapted to detect a different target sequence, and a particular reaction vessel may include any one or more of the fluorescent probes. Each probe advantageously responds to light of a different incident wavelength and emits light of a different wavelength.

At step 806, a detection module 234 is mounted on shuttle 232. As described above, detection module 234 may include any number of detection channels (i.e., excitation/detection pairs). In one embodiment, detection module 234 includes four detection channels. Each channel is optimized for a different one of the fluorescent probes included in reaction vessels 616.

At step 808, reaction vessels 616 are placed into sample wells 210 of sample unit 202. At step 810, lid assembly 112 is closed and positioned in base unit 110.

At step 812 each channel of detection module 234 is calibrated. Calibration is performed by operating stepper motors 302, 316 to position detection module 234 such that at least one of its channels is in optical communication with a calibration location 222. As described above, each calibration location provides a known fluorescent response. Accordingly, calibration measurements can be used to correct subsequent sample measurements for variations or fluctuations in detector response. Numerous calibration techniques are known in the art. Where detection module 234 has multiple channels, each channel may be independently calibrated.

At step 814, a PCR cycle is performed. In general, step 814 involves operation of base unit 110 to regulate the temperature of sample unit 202, thereby holding the reaction vessels at desired temperatures for desired lengths of time to complete a two-step or three-step PCR cycle. Base unit 110 may be controlled via user interface 116 or by an external computer.

At step 816, fluorometer assembly 206 scans and interrogates the reaction vessels 616. The operation of fluorometer assembly 206 is advantageously controlled by an external computer and synchronized with the operation of base unit 110, so that measurements are identifiable as corresponding to particular times in the PCR process.

More specifically, at step 816a, stepper motors 302, 316 or other motion devices are operated to position detection module 234 such that each of the four detector channels is in optical communication with a different one of sample wells 210 via respective optical windows 502, 504, 506, 508. At step 816b, the LED or other light source for each channel is activated (flashed on for a brief period) to stimulate fluorescence. In one embodiment, the LEDs of different channels are operated in parallel; in an alternative embodiment, they are operated sequentially so as to avoid reflected LED light from one channel causing false signals in the photodetector of another channel.

At step 816c, resulting fluorescence is detected by the corresponding photodiode or other detector of the channel, which is read out to the external computer. The detectors may be read out in various ways. For instance, a peak signal may be detected, the signal may be integrated over a time interval, or the decay of the fluorescent signal after the LED has been deactivated may be measured.

Steps 816a-c are advantageously repeated, with the position of the detection module being changed each time so that each channel of detection module 234 eventually interrogates each of the sample wells 210. In one embodiment, scanning and interrogating four channels for each of 96 sample wells takes about 15 seconds. The external computer advantageously executes a program (e.g., the Opticon Monitor program sold by MJ Research, Inc.) that enables a user to view measurement data as they are collected, in graphical and/or tabular form. Such programs are well known in the art. An example includes the Opticon Monitor™ program sold by MJ Research, Inc.

Steps 814 and 816 may be repeated for any number of reaction cycles. Persons of ordinary skill in the art will recognize that real-time fluorescence measurements from process 800 may be used to detect and quantify the presence of each target sequence. Such measurements may also be used for purposes such as determining reaction rates and adjusting reaction parameters for improved efficiency, as well as determining when additional reaction cycles are no longer needed in a particular experiment (e.g., when a sufficient quantity of a target sequence has been produced).

It will be appreciated that process 800 is illustrative and that variations and modifications are possible. Steps described as sequential may be executed in parallel, order of steps may be varied, and steps may be modified or combined. For example, fluorescence measurements may be performed at any point during a PCR cycle, performed multiple times during each PCR cycle (including substantially continuous scanning of the sample wells), or not performed until after some number of PCR cycles. Any number of distinguishable fluorescent probes may be used in a single reaction vessel, and the detection module may be adapted to include at least as many channels as the number of probes in use. In some embodiments, the detection module includes multiple channels optimized for the same probe. This may reduce the scanning time since only one of these channels needs to be used to interrogate a particular sample well.

In addition, as mentioned above, in one alternative embodiment, the various channels of detection module 234 are arranged such that when one of its channels is in optical communication with a sample well 210, other channels are not. This arrangement allows for a "flyover" mode of operation, in which detection module 234 is substantially continuously in motion during a scanning pass over the wells. Crosstalk between the channels is reduced because only one sample well at a time receives any excitation light.

CONCLUSION

While the invention has been described with respect to specific embodiments, one skilled in the art will recognize that numerous modifications are possible. For instance, the fluorescence detection assembly described herein may be adapted for use with a wide variety of thermal cycler systems and may interrogate sample wells from any direction (e.g., above or below) in accordance with the design of a particular instrument. In addition, the system may be adapted to detect a wide range of molecules of biological interest that are identifiable by a fluorescent label or probe; it is not limited to nucleic acids or to any particular amplification process.

Thus, although the invention has been described with respect to specific embodiments, it will be appreciated that the invention is intended to cover all modifications and equivalents within the scope of the following claims.

What is claimed is:

1. A fluorescence detection apparatus for analyzing samples located in a plurality of wells in a thermal cycler, the apparatus comprising:
   a support structure attachable to the thermal cycler;
   a shuttle movably mounted on the support structure; and
   a detection module attached to the shuttle, the detection module including:
      a housing having an opening oriented toward the plurality of wells;
      an excitation light generator disposed within the housing; and
      an emission light detector disposed within the housing,
   wherein, when the support structure is attached to the thermal cycler, a heating element is disposed between the detection module and the sample wells and the shuttle is movable to position the detection module in optical communication with different wells of the plurality of wells through a plurality of openings extending through the heating element.

2. The fluorescence detection apparatus of claim 1 wherein an excitation optical path from the excitation light generator to the opening has a fixed length and a detection optical path from the opening to the emission light detector has a fixed length.

3. The fluorescence detection apparatus of claim 1 further comprising:
   a calibration element disposed such that the detection module is movable so as to be positioned in optical communication with the calibration element,
   wherein the calibration element provides a known fluorescence response.

4. The fluorescence detection apparatus of claim 3 wherein the calibration element is located between two or more of the plurality of wells.

5. The fluorescence detection apparatus of claim 3 wherein the calibration element is located in an area peripheral to the plurality of wells.

6. The fluorescence detection apparatus of claim 1 wherein positioning of the detection module with respect to the wells is controlled by an external computer.

7. The fluorescence detection apparatus of claim 1 wherein operation of the excitation light generator and the emission light detector is controlled by an external computer.

8. The fluorescence detection apparatus of claim 1 wherein the detection module is detachably attached to the shuttle.

9. The fluorescence detection apparatus of claim 1 wherein the excitation light generator comprises a light-emitting diode.

10. The fluorescence detection apparatus of claim 1 further comprising at least two stepper motors mounted on the support structure, the stepper motors being operative to move the shuttle in at least two dimensions.

11. The fluorescence detection apparatus of claim 1 wherein the detection module includes at least two emission light detectors.

12. The fluorescence detection apparatus of claim 1 wherein the detection module includes at least two excitation light generators.

13. A thermal cycler apparatus comprising:
   a thermal cycler having an exterior housing and a plurality of sample wells for holding reaction vessels;
   a heater to prevent condensation from forming on a surface of the reaction vessels when the reaction vessels are in the sample wells, the heater having a plurality of transparent portions to permit optical communication with each of the plurality sample wells;
   a support structure disposed inside the exterior housing on an opposite side of the heater from the sample wells;
   a shuttle movably mounted on the support structure; and
   a detection module attached to the shuttle, the detection module including:
      a module housing having an opening that is oriented toward the plurality of sample wells when the thermal cycler is in an operating state;
      an excitation light generator disposed entirely within the module housing; and
      an emission light detector disposed entirely within the module housing;
   wherein, when the thermal cycler is in the operating state, the shuttle is movable to position the detection module in optical communication with different sample wells of the plurality of sample wells through the transparent portions of the heater.

14. The thermal cycler apparatus of claim 13 wherein the excitation light generator comprises a light-emitting diode.

15. The thermal cycler apparatus of claim 13 further comprising at least two stepper motors mounted on the support structure, the stepper motors being operative to move the shuttle in at least two dimensions.

16. The thermal cycler apparatus of claim 13 further comprising a fitting on an exterior surface of the housing of the detection module, the fitting adapted to attach the detection module to the shuttle, wherein the fitting provides only electrical and mechanical connections.

17. The thermal cycler apparatus of claim 13 wherein the detection module includes at least two emission light detectors.

18. The thermal cycler apparatus of claim 13 wherein the detection module includes at least two excitation light generators.

19. The thermal cycler apparatus of claim 13 wherein movement of the shuttle and operation of the excitation light generator and the emission light detector are controlled by an external computer such that emission light is measured while the shuttle is in motion.

20. The thermal cycler apparatus of claim 13 further comprising:
   a plurality of optical components defining an excitation optical path for light of an excitation wavelength from the excitation light generator to the opening of the housing and a detection optical path for light of a detection wavelength from the opening of the housing to the emission light detector,
   wherein all of the optical components of the excitation optical path and the detection optical path are disposed within the housing of the detection module.

21. The thermal cycler apparatus of claim 13 wherein the detection module is positioned such that the opening is below the plurality of sample wells.

22. The thermal cycler apparatus of claim 13 wherein the plurality of transparent portions of the heater includes a plurality of holes extending through the heater and aligned with the sample wells.

* * * * *